United States Patent

Dralle-Voss et al.

Patent Number: 5,376,155
Date of Patent: Dec. 27, 1994

[54] MINERAL OIL MIDDLE DISTILLATE COMPOSITIONS

[75] Inventors: Gabriele Dralle-Voss, Darmstadt; Knut Oppenlaender, Ludwigshafen; Klaus Barthold, Mannheim; Bernd Wenderoth, Lampertheim; Wolfgang Kasel, Nussloch, all of Germany

[73] Assignee: BASF Aktiengesellschaft, Ludwigshafen, Germany

[21] Appl. No.: 145,598

[22] Filed: Nov. 4, 1993

[30] Foreign Application Priority Data

Nov. 7, 1992 [DE] Germany ............... 4237662

[51] Int. Cl.$^5$ ............................... C10L 1/22
[52] U.S. Cl. ........................ 44/408; 44/418; 44/419
[58] Field of Search ............ 44/399, 408, 418, 419

[56] References Cited

U.S. PATENT DOCUMENTS

| | | |
|---|---|---|
| 3,048,479 | 8/1962 | Ilnyckyl et al. |
| 3,173,770 | 3/1965 | Thompson et al. ......... 44/419 X |
| 3,202,491 | 8/1965 | Maxwell et al. ............ 44/419 X |
| 3,407,051 | 10/1968 | Thompson et al. ......... 44/419 X |
| 3,455,665 | 7/1969 | Andres ......................... 44/419 |
| 3,981,850 | 9/1976 | Wisotsky et al. |
| 5,071,445 | 12/1991 | Oppenlaender et al. |

FOREIGN PATENT DOCUMENTS 2095698 10/1982 United Kingdom.

*Primary Examiner*—Prince Willis, Jr.
*Assistant Examiner*—Cephia D. Toomer
*Attorney, Agent, or Firm*—Keil & Weinkauf

[57] ABSTRACT

Mineral oil middle distillate compositions based on hydrocarbon mixtures whose boiling range begins at above 160° C. and ends at below 420° C. contain, as paraffin dispersants, reaction products of aminoalkylenecarboxylic acids with primary or secondary long-chain amines.

3 Claims, No Drawings

MINERAL OIL MIDDLE DISTILLATE COMPOSITIONS

The present invention relates to mineral oil middle distillate compositions based on a hydrocarbon mixture which contain, as a paraffin dispersant, a reaction product of an aminoalkylenecarboxylic acid with primary or secondary long-chain amines.

Middle distillates, for example gas oils, diesel oils or fuel oils, which are obtained by distillation from mineral oils have different contents of paraffins, depending on the origin of the crude oil. Solid paraffins separate out at relatively low temperatures (cloud point, CP). On further cooling, the lamellar n-paraffin crystals form a "house-of-cards structure" and the middle distillate sets although the predominant part of the middle distillate is still liquid. The flowability of the mineral oil middle distillates is considerably adversely affected by the precipitated n-paraffins in the temperature range between the cloud point and pour point. The paraffins block filters and cause nonuniform fuel feed to the combustion units or completely stop this feed.

It has long been known that the crystal growth of the paraffins in the mineral oil middle distillates can be modified by suitable additives. Effective additives on the one hand prevent middle distillates from forming such house-of-cards structures and becoming solid at temperatures a few degrees Centigrade below the temperature at which the first paraffin crystals crystallize out and, on the other hand, form fine, well crystallized, separate paraffin crystals which pass through filters in motor vehicles and heating units or at least form a filter cake which is permeable to the liquid part of the middle distillates, so that trouble-free operation is ensured.

A disadvantage of this prior art is based on the fact that, because they have a higher density than the liquid part, the precipitated paraffin crystals show an increasing tendency to settle on the bottom of the container during storage. This results in the formation of a phase which is homogeneous in the upper part of the container and has a low paraffin content, and a two-phase paraffin-rich layer at the bottom. Since both in vehicle tanks and in storage or delivery tanks of the mineral oil dealers the middle distillate is generally taken off slightly above the bottom of the tank, there is a danger that the high concentration of solid paraffins will lead to blockage of filters and metering apparatuses. This danger is the greater the further the storage temperature falls below the precipitation temperature of the paraffins (cloud point), since the amount of paraffin which separates out is a function of the temperature and increases with decreasing temperature.

The paraffin crystal modifiers, is the flow improvers, are polymers which change the crystal growth of the n-paraffins by crystallization (interaction). The flow properties of the middle distillate are advantageously affected at relatively low temperatures. According to DIN 51,428, the efficiency of the flow improvers is expressed indirectly by measurement of the cold filter plugging point (CFPP).

The conventional ethylene copolymers, especially copolymers of ethylene and unsaturated esters, are used as cold flow improvers. DE 11 47 799 and DE 19 14 756 describe, for example, copolymers of ethylene with vinyl acetate, containing from 25 to 45% by weight of vinyl acetate or vinyl propionate and having a molecular weight of from 500 to 5,000.

Furthermore, GB 2 095 698 discloses that a combination of the stated copolymers with amides of long-chain chain amines and aromatic or cycloaliphatic carboxylic acids can be added to middle distillates.

However, these mixtures are still unsatisfactory with regard to the dispersing properties of the paraffin which has separated out.

It is therefore necessary that the additives introduced also disperse the paraffin which has separated out.

EP 398 101-A discloses reaction products of aminoalkylenepolycarboxylic acids with long-chain secondary amines, which have been completely converted with the sine to the amide or ammonium salt, as paraffin dispersants. To achieve good dispersing of the paraffins which have separated out by means of these products, however, frequently from 0.25 to 40 ppm of a conductivity improver have to be added to the diesel fuel, in addition to the dispersant.

However, the introduction of a further additive is disadvantageous for production and is expensive. Furthermore, admixing a conductivity improver may be ecologically disadvantageous, It is an object of the present invention to provide paraffin dispersants for mineral oil middle distillates, which dispersants have an excellent dispersing effect even without additional conductivity improvers.

We have found that this object is achieved by mineral oil middle distillate compositions based on a hydrocarbon mixture whose boiling range begins at above 160° C. and ends at below 420° C., containing an amount, effective as a paraffin dispersant, of compounds of the formulae I and/or II

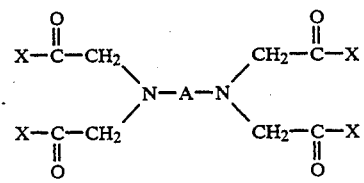

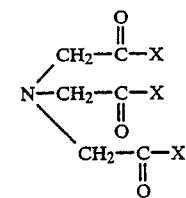

where
A is straight-chain or branched alkylene of 2 to 6 carbon atoms or a radical of the formula III

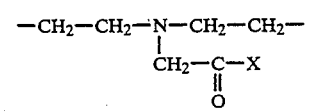

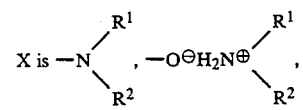

—OH and/or —O⊖M⊕ $R^1$ is hydrogen or a straight-chain aliphatic radical of 10 to 30 carbon atoms, $R^2$ is a straight-chain aliphatic radical of 10 to 30 carbon atoms and M is an alkali metal or alkaline earth metal, with the proviso that the following two conditions are fulfilled, is. X is a) at least one

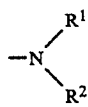

group and b) at least one —OH— and/or —O⊖M⊕ group.

Surprisingly, we have found that, when the compounds of the formulae I and/or II, i.e. the reaction products of aminoalkylenecarboxylic acids (III and IV)

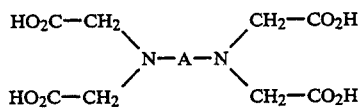

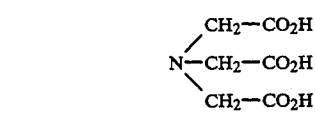

where A has the abovementioned meanings, with primary or secondary long-chain amines having at least one amide and one carboxyl and/or carboxylate group, are used, it is possible to dispense with the addition of a conductivity improver in order to obtain the same effects in the dispersing of the paraffins which have separated out.

The novel mineral oil middle distillate compositions thus have improved cold flow due to better dispersing of the paraffin crystals which have separated out.

In the compounds of the formulae I and/or II which are used in the mineral oil middle distillates, $R^1$ is preferably hydrogen or $R^1$ and $R^2$ are each preferably a straight-chain aliphatic radical of 14 to 22 carbon atoms. Particularly preferably, both $R^1$ and $R^2$ are a straight-chain aliphatic radical of 10 to 30, in particular 14 to 22, carbon atoms, is the amines used for the preparation of the compounds are secondary amines. Specific examples of secondary amines are dioleylamine, di-tallow fatty amine, dipalmitamine, dicocosamine and dibehenylamine and preferably distearylamine or hydrogenated di-tallow fatty amine (the latter usually being of 16 to 18 carbon atoms).

The aminoalkylenepolycarboxylic acid (III, IV) is advantageously reacted with the amine in a ratio of from 1:1.5 to 1:3.

The unconverted carboxyl groups may be present as free carboxylic acids or as carboxylates which are formed either by intramolecular neutralization with the aminoalkylene groups (betaine formation) or by neutralization with metal salts:

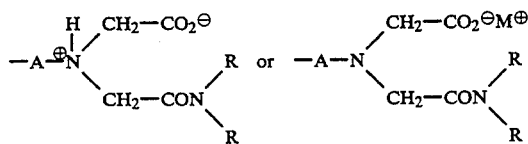

Compounds of the formula V

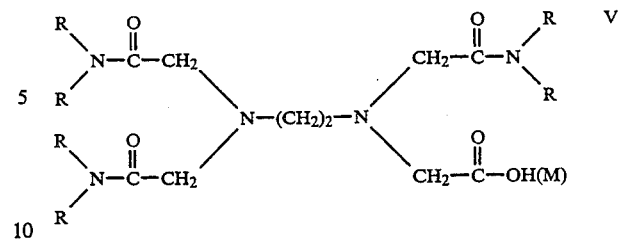

i.e. where three radicals X are each

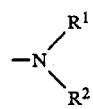

and one radical X is —OH or —O⊖M⊕, are particularly preferred.

The compounds of the formulae I and II are generally added to the novel mineral oil middle distillate compositions in amounts of from 25 to 1,000 ppm, preferably from 50 to 500 ppm.

The middle distillates usually contain conventional flow improvers which are described in detail in the patent literature, for example in DE 19 14 756 and DE 40 36 227 (ethylene/vinyl ester copolymers and mixtures thereof with other copolymers), EP 214 876 (α-olefin/maleic anhydride ester) or EP 155 807 (alkyl fumarate/vinyl acetate copolymers).

However, terpolymers which, in addition to ethylene and vinyl esters or acrylates, also contain further comonomers are also suitable. The molecular weight of these flow improvers is as a rule from 500 to 5,000, preferably from 1,000 to 3,000.

Mixtures of different flow improvers are also suitable.

EXAMPLES

A) Synthesis of the aminoalkylenepolycarboxamides PD1: Preparation of the trisamide of ethylenediaminetetraacetic acid and distearylamine: 1,010.2 g (2 mol) of distearylamine PD (hydrogenated ditallow fatty amine) are melted, and 6 g of p-toluenesulfonic acid and 194.6 g (0.67 mol) of ethylenediaminetetraacetic acid are added.

The reaction mixture is heated to 190° C. and is condensed for 3 hours at this temperature. The product is then filtered while hot. 1,180 g of a brown solid having an acid number of 33 mg KOH/g are obtained. PD2: Preparation of the calcium salt of PD1

101 g (0.2 mol) of PD1) are melted, and 14.8 g of calcium hydroxide are added. Heating is carried out for 2 hours at 100° C., after which the product is filtered. About 110 g of a brown solid are obtained.

B) Testing of the mineral oil middle distillate compositions

Description of the test method:

Various amounts of paraffin dispersants PD 1, PD 2 and PD 3 and/or flow improvers F1, and if necessary also conductivity improvers CI (E) (comparison), were added to the middle distillates at 40° C. while stirring, after which the mixture was cooled to room temperature.

The additive-containing middle distillates were stored in 100 ml measuring cylinders for 20 hours in a refrigerator at −13° C. Thereafter, the volume of the paraffin phase which had settled out (% by volume) was visually estimated and the appearance of the oil phase was assessed.

The following mineral oil middle distillate compositions were tested: Mineral oil middle distillate compositions containing 1) as a paraffin dispersant PD 1, PD 2 ethylenediaminetetraacetic acid derivatives according to A),
2) as flow improver Fl 1 ethylene/vinyl propionate, containing about 40% by weight of vinyl propionate and having an average molecular weight of about 2,500

C) Mineral oil middle distillate compositions (comparison according to EP 398 101) containing 1) as a paraffin dispersant PD 3 nitriloacetamide A) 1 from EP 398 101
2) as flow improver Fl 1 ethylene/vinyl propionate, containing about 40% by weight of vinyl propionate and having an average molecular weight of about 2,500
3) as conductivity improver CI (E) from EP 398 101

Diesel fuels of commercial German refinery quality were used as middle distillates for the following dispersion tests; they are referred to as DK 1, DK 2 and DK 3:

|  | DK 1 | DK 2 | DK 3 |
| --- | --- | --- | --- |
| Cloud point CP (°C.) | −8 | −8 | −7 |
| CFPP (°C.) | −13 | −12 | −10 |
| Density at 20° C. (g/ml) | 0.827 | 0.831 | 0.829 |
| Beginning of boiling range (°C.) | 165 | 175 | 183 |
| 20% boiling point (°C.) | 210 | 223 | 211 |
| 90% boiling point (°C.) | 318 | 314 | 317 |
| End of boiling range (°C.) | 358 | 352 | 364 |

The results are shown in Tables 1 to 3. It is evident that the compounds PD 1 and PD 2 have a better dispersing effect than the compound which is disclosed in EP 398 101 which has comparable dispersing effects only in the presence of a conductivity improver.

TABLE 1

DK 1, CP: −8° C., CFPP: −13° C.

| PD 1 (ppm) | PD 2 (ppm) | PD 3 (ppm) | Fl 1 (ppm) | CI (E) (ppm) | Paraffin sediment (% by vol.) | Appearance of oil phase |
| --- | --- | --- | --- | --- | --- | --- |
| 100 | — | — | 200 | — | 0 | dispersed |
| — | — | 100 | 200 | 1 | 35 | dispersed |

TABLE 2

DK 2, CP: −8° C., CFPP: −12° C.

| PD 1 (ppm) | PD 2 (ppm) | PD 3 (ppm) | Fl 1 (ppm) | CI (E) (ppm) | Paraffin sediment (% by vol.) | Appearance of oil phase |
| --- | --- | --- | --- | --- | --- | --- |
| 100 | — | — | 300 | — | 15 | dispersed |
| — | 100 | — | 300 | — | 20 | dispersed |
| — | — | 100 | 300 | 1 | 30 | dispersed |
| — | — | 100 | 300 | — | 25 | cloudy |
| — | — | — | 300 | — | 35 | clear |

TABLE 3

DK 3, CP: −7° C., CFPP: −10° C.

| PD 1 (ppm) | PD 2 (ppm) | PD 3 (ppm) | Fl 1 (ppm) | CI (E) (ppm) | Paraffin sediment (% by vol.) | Appearance of oil phase |
| --- | --- | --- | --- | --- | --- | --- |
| 100 | — | — | 300 | — | 20 | dispersed |
| — | 100 | — | 300 | — | 10 | dispersed |
| — | — | 100 | 300 | 1 | 15 | dispersed |
| — | — | 100 | 300 | — | 10 | cloudy |
| — | — | — | 300 | — | 10 | clear |

We claim:
1. A mineral oil middle distillate composition based on a hydrocarbon mixture whose boiling range begins at above 160° C. and ends at below 420° C., containing an amount, effective as a paraffin dispersant, of a compound of the formulae I or II

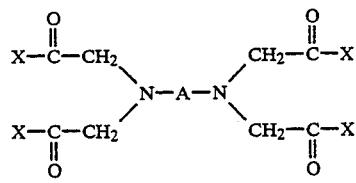

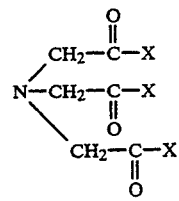

where A is straight-chain or branched alkylene of 2 to 6 carbon atoms or a radical of the formula III

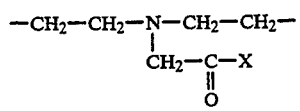

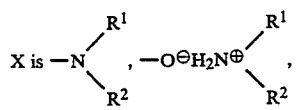

—OH or —O⊖M⊕ $R^1$ is hydrogen or a straight-chain aliphatic radical of 10 to 30 carbon atoms, $R^2$ is a straight-chain aliphatic radical of 10 to 30 carbon atoms and M is an alkali metal or alkaline earth metal, with the proviso that the following two conditions are fulfilled, i.e. X is a) at least one

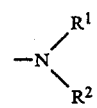

group and
b) at least one —OH— or —O⊖M⊕ group.
2. A mineral oil middle distillate composition as defined in claim 1, wherein $R^1$ and $R^2$ are each a straight-chain aliphatic radical of 14 to 22 carbon atoms.
3. A mineral oil middle distillate composition as defined in claim 1, wherein $R^1$ and $R^2$ are each a straight-chain aliphatic radical of 16 to 18 carbon atoms.

* * * * *

UNITED STATES PATENT AND TRADEMARK OFFICE
CERTIFICATE OF CORRECTION

PATENT NO.: 5,376,155

DATED: December 27, 1994

INVENTOR(S): DRALLE-VOSS et al.

It is certified that error appears in the above-identified patent and that said Letters Patent is hereby corrected as shown below:

Claim 1, column 6, line 47, delete "hydrogen or".

Signed and Sealed this

Seventh Day of March, 1995

Attest:

BRUCE LEHMAN

Attesting Officer

Commissioner of Patents and Trademarks